United States Patent
Niida et al.

(10) Patent No.: US 9,629,530 B2
(45) Date of Patent: Apr. 25, 2017

(54) ENDOSCOPE APPARATUS WITH COLOR-BALANCE MEASURING AND COLOR-BALANCE CORRECTING

(71) Applicant: OLYMPUS CORPORATION, Tokyo (JP)

(72) Inventors: Koichi Niida, Hachioji (JP); Atsuhiko Kushida, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/070,150

(22) Filed: Mar. 15, 2016

(65) Prior Publication Data

US 2016/0192834 A1  Jul. 7, 2016

Related U.S. Application Data

(63) Continuation of application No. PCT/JP2014/078101, filed on Oct. 22, 2014.

(30) Foreign Application Priority Data

Oct. 25, 2013  (JP) .................................. 2013-222328

(51) Int. Cl.
*A61B 1/06* (2006.01)
*A61B 1/04* (2006.01)
(Continued)

(52) U.S. Cl.
CPC ........ *A61B 1/0676* (2013.01); *A61B 1/00009* (2013.01); *A61B 1/045* (2013.01);
(Continued)

(58) Field of Classification Search
CPC ..... A61B 1/0676; A61B 1/0009; A61B 1/045; A61B 1/06; A61B 1/0684; G02B 23/2461; H04N 5/2256; H04N 9/041
(Continued)

(56) References Cited

U.S. PATENT DOCUMENTS

| 4,713,683 A | * | 12/1987 | Fujimori | ............. A61B 1/0638 348/269 |
| 5,864,361 A | | 1/1999 | Sekiya et al. | |
| 8,018,485 B2 | | 9/2011 | Minai et al. | |

FOREIGN PATENT DOCUMENTS

| EP | 2338404 A1 | 6/2011 |
| JP | H08-126607 A | 5/1996 |

(Continued)

OTHER PUBLICATIONS

International Search Report dated Jan. 20, 2015 issued in PCT/JP2014/078101.

(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An endoscope apparatus includes a CCD disposed at a distal end portion of an endoscope insertion section, a first LED and a second LED functioning as illumination-light emitting unit, a region setting section that sets a first region where illumination by the first LED is predominant on an endoscopic image and a second region where illumination by the second LED is predominant on the endoscopic image, and a white balance circuit that respectively calculates color balance values corresponding to the first and second regions and applies correction processing to a color balance value of a video signal of the entire endoscopic image on the basis of results of the respective calculations.

11 Claims, 11 Drawing Sheets

(51) Int. Cl.
  *H04N 5/225*  (2006.01)
  *A61B 1/00*  (2006.01)
  *G02B 23/24*  (2006.01)
  *H04N 9/73*  (2006.01)
  *A61B 1/045*  (2006.01)

(52) U.S. Cl.
  CPC ........ *A61B 1/0684* (2013.01); *G02B 23/2461* (2013.01); *H04N 5/2256* (2013.01); *H04N 9/735* (2013.01); *H04N 2005/2255* (2013.01)

(58) Field of Classification Search
  USPC ............... 600/109, 160, 178, 179, 180, 181; 348/65
  See application file for complete search history.

(56) References Cited

FOREIGN PATENT DOCUMENTS

| | | |
|---|---|---|
| JP | 2005-296200 A | 10/2005 |
| JP | 2009-273676 A | 11/2009 |
| JP | 2011-217969 A | 11/2011 |
| WO | WO 2010/044483 A1 | 4/2010 |

OTHER PUBLICATIONS

Japanese Office Action dated Jul. 7, 2015 issued in JP 2015-516320.

\* cited by examiner

ENDOSCOPE APPARATUS WITH COLOR-BALANCE MEASURING AND COLOR-BALANCE CORRECTING

CROSS REFERENCE TO RELATED APPLICATION

This application is a continuation application of PCT/JP2014/078101 filed on Oct. 22, 2014 and claims benefit of Japanese Application No. 2013-222328 filed in Japan on Oct. 25, 2013, the entire contents of which are incorporated herein by this reference.

BACKGROUND OF THE INVENTION

1. Field of the Invention

The present invention relates to an endoscope apparatus and, more particularly, to an endoscope apparatus including an endoscope in which a plurality of illuminating means such as LEDs are provided at a distal end of an endoscope insertion section.

2. Description of the Related Art

An electronic endoscope in which an LED is provided as illuminating means at a distal end of an endoscope insertion section has been disclosed in, for example, Japanese Patent Application Laid-Open Publication No. 2011-217969. Further, in recent years, an electronic endoscope in which a plurality of LEDs are provided as the illuminating means at the distal end of the endoscope insertion section has also been proposed.

In the electronic endoscope in which the plurality of LEDs are provided at the distal end of the endoscope insertion section, color temperatures of radiated lights of the plurality of LEDs are sometimes different from one another because of factors such as variation in characteristics of the mounted plurality of LEDs or variation in driving conditions of the LEDs.

In an endoscope in which a light guide for guiding illumination light generated in a light source device to an endoscope distal end is provided, when a plurality of illuminating means are provided at a distal end of an endoscope insertion section, a phenomenon same as the above occurs because of a factor such as variation in light guide characteristics or variation in optical component characteristics in guiding the illumination light to the light guide.

SUMMARY OF THE INVENTION

An endoscope apparatus according to an aspect in the present invention includes: an endoscope insertion section to be inserted into a subject; a first light emitting element that generates first illumination light for the subject; a second light emitting element that generates second illumination light for the subject; a first illumination optical system disposed at a distal end portion of the endoscope insertion section to emit the first illumination light to the subject; a second illumination optical system disposed at the distal end portion of the endoscope insertion section to emit the second illumination light to the subject from a position different from an emitting position of the first illumination light by the first illumination optical system; an image pickup section that picks up an optical image of the subject illuminated by the first and second illumination lights; a region setting section that sets, on the basis of a video signal related to the optical image of the subject picked up by the image pickup section, a first region where illumination by the first illumination light is predominant on an endoscopic image related to the video signal and a second region where illumination by the second illumination light is predominant on the endoscopic image; a first color-balance measuring section that measures a color balance of the video signal corresponding to the first region and calculates a first color balance value; a second color-balance measuring section that measures a color balance of the video signal corresponding to the second region and calculates a second color balance value; and a color-balance correcting section that applies, on the basis of the first and second color balance values, correction processing to each of the video signal corresponding to the first region and the video signal corresponding to the second region to set an entirety of the endoscopic image to a predetermined color balance.

DETAILED DESCRIPTION OF THE PREFERRED EMBODIMENTS

Embodiments of the present invention are described below with reference to the drawings.

(First Embodiment)

Figure 1:
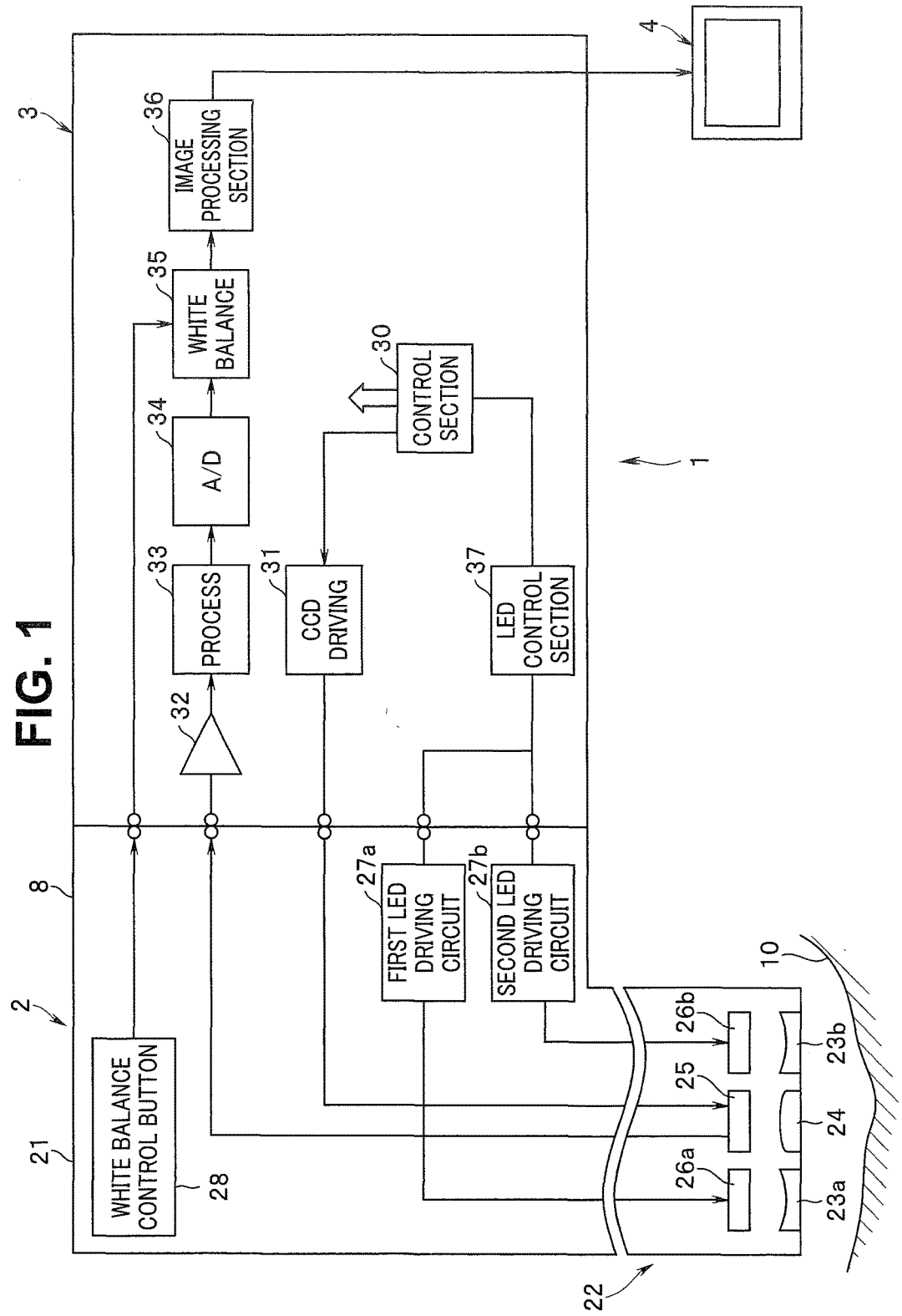
FIG. 1 is a diagram showing an overall configuration of an endoscope apparatus according to a first embodiment of the present invention.
Figure 2:
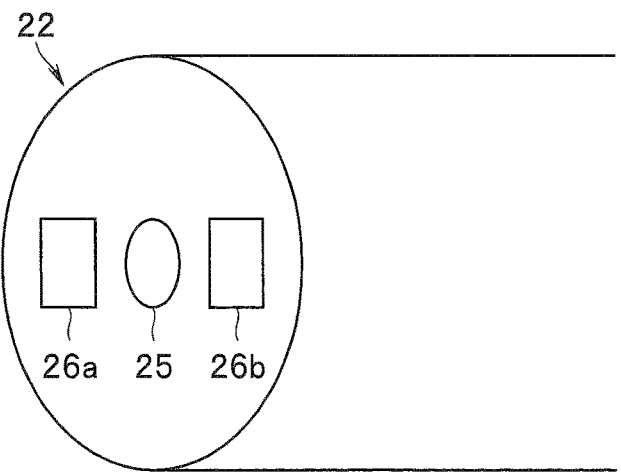
FIG. 2 is a diagram schematically showing a configuration of a distal end portion of an endoscope insertion section in the endoscope apparatus according to the first embodiment.

FIG. 1 is a diagram showing an overall configuration of an endoscope apparatus according to a first embodiment of the present invention. FIG. 2 is a diagram schematically showing a configuration of a distal end portion of an endoscope insertion section in the endoscope apparatus according to the first embodiment.

An endoscope apparatus 1 includes, as shown in FIG. 1, an electronic endoscope (hereinafter abbreviated as endoscope) 2 that is insertable into a body cavity and picks up an image of an observation target part 10 such as a diseased part in the body cavity and outputs an image pickup signal, a video processor 3 that is connected to the endoscope 2 and applies signal processing or the like to the image pickup signal outputted from the endoscope 2 to thereby output a video signal, and a monitor 4 that is connected to the video processor 3 and displays an output image corresponding to the video signal outputted from the video processor 3.

The endoscope 2 includes an elongated insertion section 22 inserted into the body cavity and an operation section 21 provided on a rear end side of the insertion section 22. The endoscope 2 is connected to the video processor 3 via a universal cord 8 extended from the operation section 21.

In the operation section 21, for example, a white balance control button 28 and a not-shown group of other scope switches capable of outputting predetermined instruction signals to the video processor 3 are provided.

In the operation section 21, a first LED driving circuit 27a and a second LED driving circuit 27b for respectively driving a first LED 26a and a second LED 26b explained in detail below are provided.

An objective lens 24 that forms an image of the observation target part 10 is disposed on a distal end face of a distal end portion of the insertion section 22. A CCD 25 is disposed in an image forming position of the objective lens 24.

The CCD 25 is driven according to a CCD driving signal outputted from the video processor 3. The CCD 25 photoelectrically converts the image of the observation target part 10 formed by the objective lens 24 and outputs the image as an image pickup signal.

The image pickup signal outputted from the CCD 25 is outputted to the video processor 3 via a signal line provided on insides of the insertion section 22 and the universal cord 8.

On the other hand, at the distal end portion of the insertion section 22, as shown in FIG. 2, the first LED 26a and the second LED 26b are symmetrically disposed across the CCD 25 as a plurality of (in the first embodiment, two) light emitting elements for illuminating the observation target part 10 in the body cavity.

On the distal end face of the distal end portion of the insertion section 22, illumination lenses 23a and 23b respectively disposed to be opposed to end faces on light emission sides of the first LED 26a and the second LED 26b are disposed. Note that, in FIG. 2, the objective lens 24 and the illumination lenses 23a and 23b disposed on the distal end face are omitted.

The first LED 26a and the second LED 26b are respectively connected to the first LED driving circuit 27a and the second LED driving circuit 27b disposed in the operation section 21. Further, both of the first LED driving circuit 27a and the second LED driving circuit 27b are connected to an LED control section 37 provided in the video processor 3.

The first LED 26a and the second LED 26b are respectively driven and controlled by the first LED driving circuit 27a and the second LED driving circuit 27b under control by the LED control section 37. Illumination lights generated by the driving control are emitted to the observation target part 10 in the body cavity after respectively passing through the illumination lenses 23a and 23b.

The video processor 3 includes a CCD driving circuit 31 that outputs the CCD driving signal for driving the CCD 25, an amplifier 32 that amplifies the image pickup signal outputted from the CCD 25, a process circuit 33 that applies signal processing such as correlated double sampling to the image pickup signal amplified by the amplifier 32, an A/D converter 34 that applies A/D conversion to the image pickup signal processed by the process circuit 33, a white balance circuit 35 that applies white balance processing to a video signal converted by the A/D converter to thereby generate color signals including an R signal, a G signal, and a B signal, and an image processing section 36 that applies predetermined image processing to a signal outputted from the white balance circuit 35 and outputs the signal to the monitor 4.

As explained above, the LED control section 37 is provided in the video processor 3. The LED control section 37 controls the first LED driving circuit 27a and the second LED driving circuit 27b disposed in the operation section 21 of the endoscope 2.

Further, the video processor 3 includes a control section 30 that controls the amplifier 32, the process circuit 33, the A/D converter 34, the white balance circuit 35, the image processing section 36, and the like and controls the CCD driving circuit 31 and the LED control section 37.

The white balance circuit 35 in the present embodiment is explained in detail below.

Figure 3:
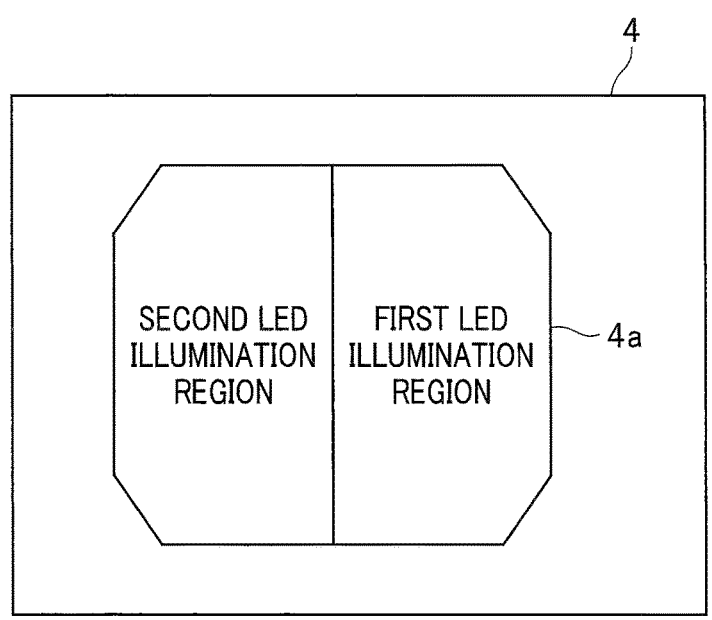
FIG. 3 is a diagram showing LED illumination regions in an endoscopic image of the endoscope apparatus according to the first embodiment.

FIG. 3 is a diagram showing LED illumination regions in an endoscopic image of the endoscope apparatus according to the first embodiment.

As explained above, the first LED 26a and the second LED 26b are respectively driven and controlled by the first LED driving circuit 27a and the second LED driving circuit 27b under the control by the LED control section 37. Further, the LED control section 37 is controlled by the control section 30 together with the white balance circuit 35.

The white balance circuit 35 detects depression of the white balance control button 28 disposed in the operation section 21 to thereby start white balance calculation processing under the control by the control section 30.

As shown in FIG. 3, the white balance circuit 35 detects information for each of color components of RGB respectively in endoscopic images corresponding to an illumination region (a first LED illumination region) related to the first LED 26a and an illumination region (a second LED illumination region) related to the second LED 26b in an entire endoscopic image 4a. That is, the white balance circuit 35 measures color balances respectively in the first LED illumination region and the second LED illumination region and calculates color balance values.

Further, the white balance circuit 35 multiplies the respective RGB values with coefficients according to necessity to set ratios of the RGB in the first LED illumination region and the second LED illumination region constant. That is, the white balance circuit 35 plays a role of an arithmetic circuit for correction that performs correction processing to set a color balance (a white balance) of a video signal of the entire endoscopic image 4a constant and adjusts the white balance.

Note that, in the present embodiment, on an endoscopic image related to the video signal, a region where illumination by the first LED 26a is relatively predominant is set as the first LED illumination region and a region where illumination by the second LED 26b is relatively predominant is set as the second LED illumination region.

The white balance calculation processing in the present embodiment is explained with reference to FIG. 1 and FIGS. 2 to 4.

Figure 4:
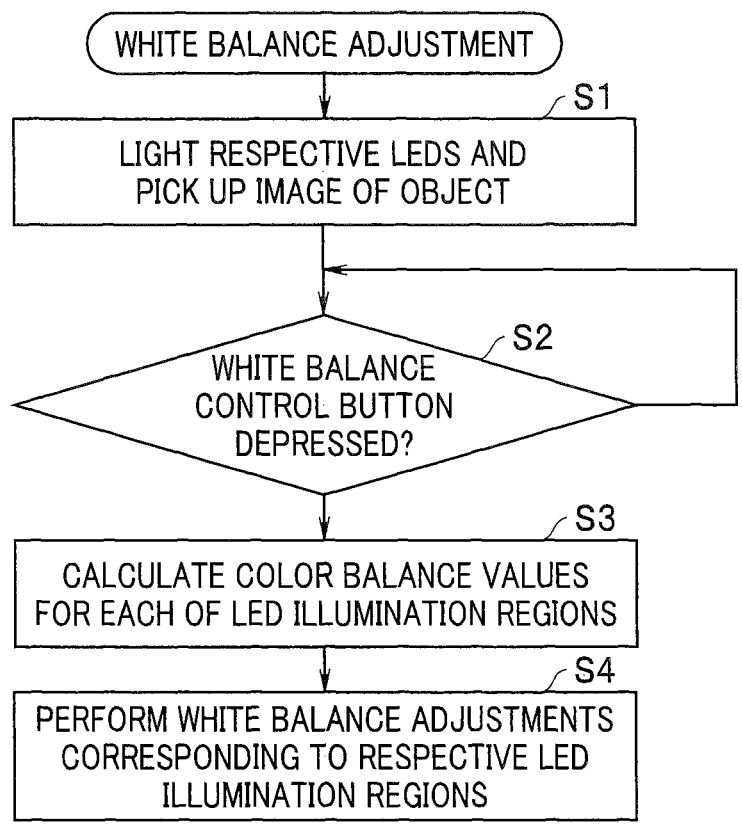
FIG. 4 is a flowchart for explaining white balance adjustment control in the endoscope apparatus according to the first embodiment.

FIG. 4 is a flowchart for explaining white balance adjustment control in the endoscope apparatus according to the first embodiment.

As shown in FIG. 4, the control section 30 controls the LED control section 37 to control the first LED driving circuit 27a and the second LED driving circuit 27b, respectively light the first LED 26a and the second LED 26b, and pick up an image of an object with the CCD 25 (step S1).

Thereafter, when the white balance control button 28 is depressed (step S2), the white balance circuit 35 detects color information corresponding to the illumination regions of the first LED 26a and the second LED 26b in an endoscopic image, measures color balances respectively in the first LED illumination region and the second LED illumination region, and calculates color balance values (step S3).

It is assumed that, as a result of the detection, the color information of the first LED illumination region and the color information of the second LED illumination region are respectively R:G:B=1:1:0.5 and 1:1:0.25. Then, the white balance circuit 35 executes the white balance calculation processing to multiply "B" with a coefficient of a double as the white balance calculation of the first LED illumination region and multiplies "B" with a coefficient of a quadruple as the white balance calculation of the second LED illumination region (step S4).

According to the white balance calculation processing, white balance adjustments respectively corresponding to the first LED illumination region and the second LED illumination region are executed.

As explained above, according to the first embodiment, according to the white balance adjustments, an effect is achieved that, even if there is variation in characteristics between the first LED 26a and the second LED 26b, which are two illuminating means, a difference in color reproduction for each of respective radiation target parts is less conspicuous.

Note that, in the present embodiment, the white balance calculation processing is performed in the first LED illumination region and the second LED illumination region. However, the number of illumination regions for detection of the color information is not limited to two. It is possible to perform highly accurate color correction by increasing the illumination regions to the number of pixels of a largest endoscopic image and calculating the color balance values for the respective regions (e.g., a second embodiment explained below).

(Second Embodiment)

An endoscope apparatus according to a second embodiment of the present invention is explained.

In the endoscope apparatus according to the first embodiment of the present invention shown in FIG. 1, the two LEDs, that is, the first LED 26a and the second LED 26b are symmetrically disposed across the CCD 25 as the illuminating means (the light emitting elements) for illuminating the observation target part 10 in the body cavity. However, in the present embodiment, four LEDs are used as light emitting elements and the number of illumination regions for detection of color information is also set to four. Other components in the second embodiment are the same as the components in the first embodiment. Only different portions are explained below. Explanation concerning portions same as the portions in the first embodiment is omitted.

Figure 5:
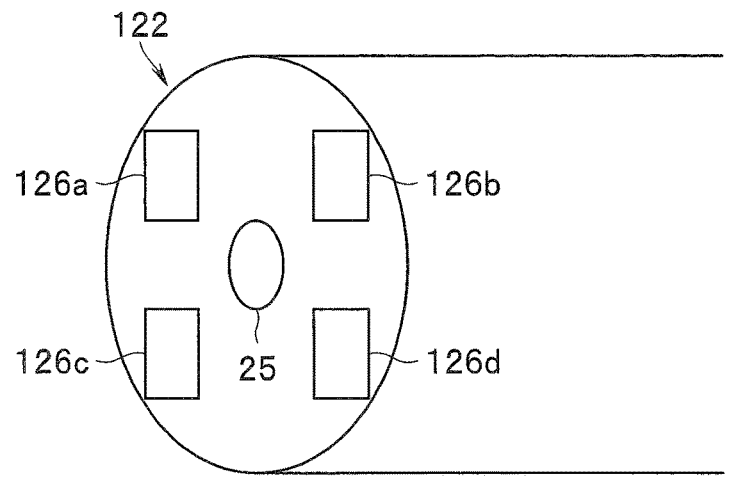
FIG. 5 is a diagram schematically showing a configuration of a distal end portion of an endoscope insertion section in an endoscope apparatus according to a second embodiment of the present invention.
Figure 6:
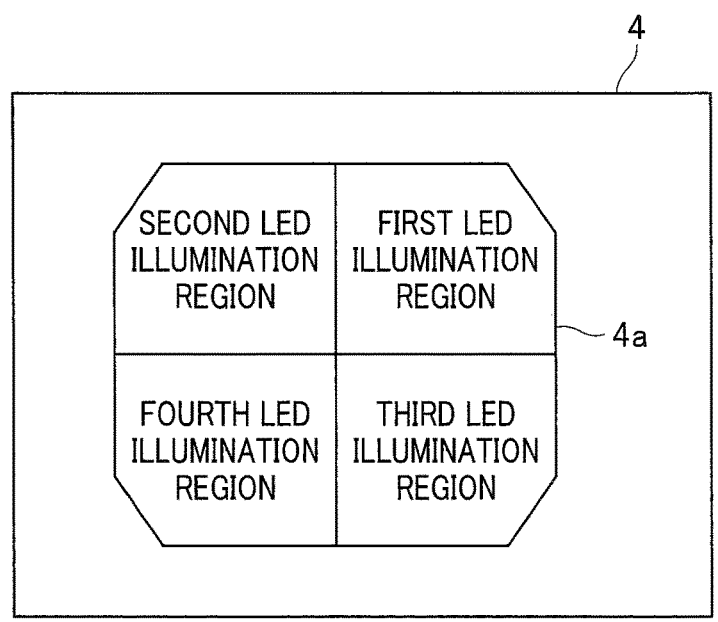
FIG. 6 is a diagram showing LED illumination regions in an endoscopic image of the endoscope apparatus according to the second embodiment.

FIG. 5 is a diagram schematically showing a configuration of a distal end portion of an endoscope insertion section in the endoscope apparatus according to the second embodiment of the present invention. FIG. 6 is a diagram showing LED illumination regions in an endoscopic image of the endoscope apparatus according to the second embodiment.

In the present embodiment, at a distal end portion of an insertion section 122, as shown in FIG. 5, as a plurality of (in the second embodiment, four) light emitting elements for illuminating the observation target part 10 in the body cavity, a first LED 126a, a second LED 126b, a third LED 126c, and a fourth LED 126d are disposed around the CCD 25.

Note that, although not shown in the figure, on a distal end face of the distal end portion of the insertion section 122, four illumination lenses respectively disposed to be opposed to end faces on light emission sides of the first LED 126a, the second LED 126b, the third LED 126c, and the fourth LED 126d are disposed. Note that, in FIG. 5 as well, the objective lens 24 and the illumination lenses disposed on the distal end face are omitted.

In the present embodiment, as in the first embodiment, the first LED 126a, the second LED 126b, the third LED 126c, and the fourth LED 126d are respectively connected to four LED driving circuits (not shown in FIG. 5) disposed in the operation section 21 to respectively correspond to the LEDs. All of the four LED driving circuits are connected to the LED control section 37 provided in the video processor 3.

The four LEDs are respectively driven and controlled by the four LED driving circuits corresponding to the LEDs under the control by the LED control section 37. Illumination lights generated by the driving control are emitted to the observation target part 10 in the body cavity after respectively passing through the illumination lenses.

In the present embodiment as well, the white balance circuit 35 detects depression of the white balance control button 28 disposed in the operation section 21 to thereby start the white balance calculation processing under the control by the control section 30.

As shown in FIG. 6, the white balance circuit 35 in the present embodiment detects information for each of color components of RGB respectively in endoscopic images corresponding to an illumination region (a first LED illumination region) related to the first LED 126a, an illumination region (a second LED illumination region) related to the second LED 126b, an illumination region (a third LED illumination region) related to the third LED 126c, and an illumination region (a fourth LED illumination region) related to the fourth LED 126d, measures color balances in the respective LED illumination regions, and calculates color balance values.

Further, the white balance circuit 35 multiplies the respective RGB values with coefficients according to necessity to set ratios of RGB in the respective LED illumination regions constant. As in the first embodiment, the white balance circuit 35 performs correction processing to set a color balance (a white balance) of a video signal of the entire endoscopic image constant and adjusts the white balance.

Note that, in the present embodiment as well, on an endoscopic image related to the video signal, a region where illumination by the first LED 126a is relatively predominant is set as the first LED illumination region, a region where illumination by the second LED 126b is relatively predominant is set as the second LED illumination region, a region where illumination by the third LED 126c is relatively predominant is set as the third LED illumination region, and a region where illumination by the fourth LED 126*d* is relatively predominant is set as the fourth LED illumination region.

The white balance calculation processing in the second embodiment is the same as the white balance calculation processing in the first embodiment. White balance adjustments respectively corresponding to the respective LED illumination regions are executed by the white balance calculation processing.

As explained above, according to the second embodiment, as in the first embodiment, an effect is achieved that, even if there is variation in characteristics between the LEDs, a difference in color reproduction for each of respective radiation target parts of the LEDs is less conspicuous.

(Third Embodiment)

An endoscope apparatus according to a third embodiment of the present invention is explained.

In the first embodiment, the white balance adjustments respectively corresponding to each of the LED illumination regions corresponding to the respective LEDs, which are the illuminating means, are executed. Therefore, even if there is variation in the characteristics between the respective LEDs, the difference in the color reproduction for each of the respective illumination target regions is made less conspicuous. However, it is also likely that, when a difference in the characteristics between the respective LEDs is large, a difference in the color reproduction for each of the illumination target regions cannot be fully corrected.

The endoscope apparatus according to the third embodiment has been devised in view of such circumstances. In addition to the white balance adjustment in the endoscope apparatus according to the first embodiment, in order to correct characteristic variation of a plurality of LEDs, which are light emitting elements functioning as illuminating means, the endoscope apparatus according to the third embodiment performs driving control of the LEDs independently from the white balance adjustment. Other components in the third embodiment are the same as the components in the first embodiment. Only different portions are explained below. Explanation concerning portions same as the portions in the first embodiment is omitted.

White balance calculation processing in the third embodiment is explained with reference to FIG. 7.

Figure 7:
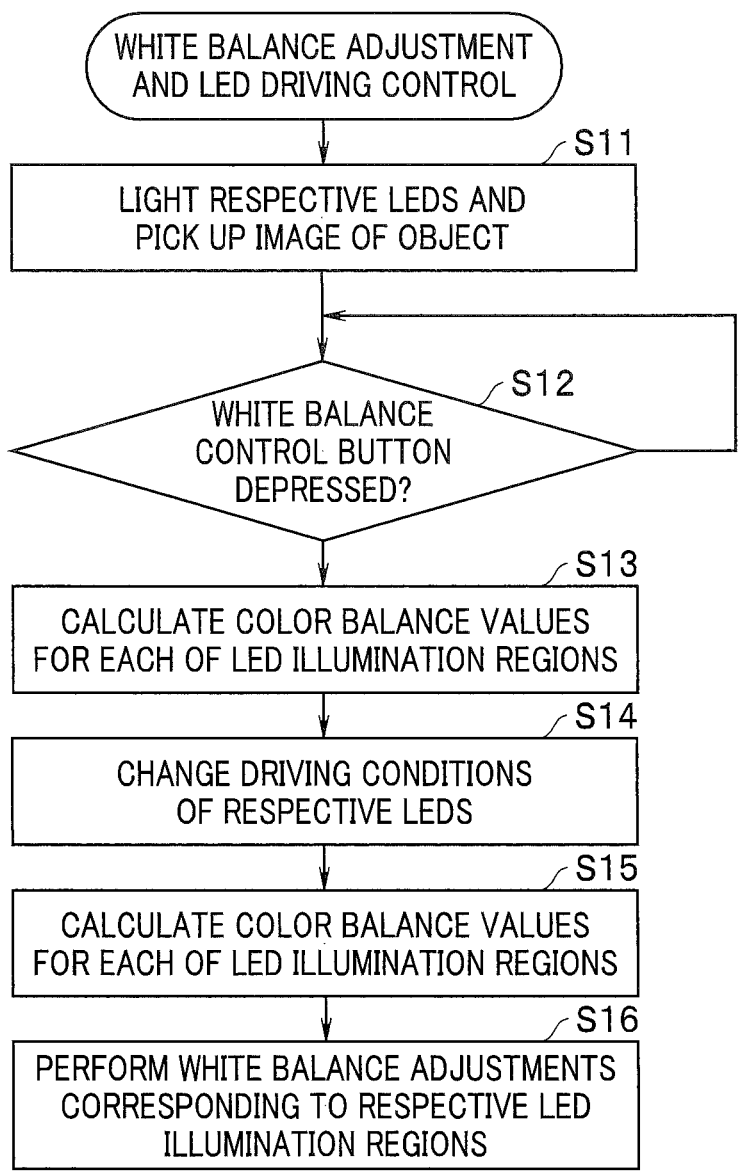
FIG. 7 is a flowchart for explaining LED driving control during white balance adjustment processing in an endoscope apparatus according to a third embodiment of the present invention.

FIG. 7 is a flowchart for explaining white balance adjustment control and LED driving control in the endoscope apparatus according to the third embodiment.

As shown in FIG. 7, the control section 30 controls the LED control section 37 to control the first LED driving circuit 27*a* and the second LED driving circuit 27*b*, respectively light the first LED 26*a* and the second LED 26*b*, and pick up an image of an object with the CCD 25 (step S11).

Thereafter, when the white balance control button 28 is depressed (step S12), the white balance circuit 35 detects color information corresponding to the illumination regions of the first LED 26*a* and the second LED 26*b* in an endoscopic image, measures color balances respectively in the first LED illumination region and the second LED illumination region, and calculates color balance values (step S13).

Subsequently, the control section 30 controls the LED control section 37 to change driving conditions of the first LED driving circuit 27*a* and the second LED driving circuit 27*b* to approximate a color balance in the first LED illumination region and a color balance in the second LED illumination region to be identical. For example, the control section 30 changes current amounts supplied to the first LED 26*a* and/or the second LED 26*b* to change light emission colors (step S14).

At this point, the control section 30 may change the current amount of one of the first LED 26*a* and the second LED 26*b* or may change the current amounts of both of the LEDs.

Thereafter, the control section 30 detects color information corresponding to the illumination regions of the first LED 26*a* and the second LED 26*b* again, measures color balances respectively in the first LED illumination region and the second LED illumination region, and calculates color balance values (step S15).

As in the first embodiment, the control section 30 executes, according to a result of the detection, white balance calculation processing same as the white balance calculation processing explained above (step S16).

According to the white balance calculation processing, white balance adjustments respectively corresponding to the first LED illumination region and the second LED illumination region are executed.

Note that, if a desired result is obtained only by changing the driving conditions of the first LED driving circuit 27*a* and the second LED driving circuit 27*b* in step S14, the white balance adjustments in step S15 and step S16 may be omitted.

As explained above, according to the third embodiment, the control of the light emission colors of the respective LEDs, which are the illuminating means, is performed in addition to the white balance adjustments in the first embodiment. Therefore, even if the variation in characteristics between the respective LEDs is large, it is possible to more accurately perform color reproduction of the entire endoscopic image.

(Fourth Embodiment)

An endoscope apparatus according to a fourth embodiment of the present invention is explained.

In the first embodiment, the white balance adjustments respectively corresponding to each of the LED illumination regions corresponding to the respective LEDs, which are the illuminating means, are executed. Therefore, even if there is variation in the characteristics between the respective LEDs, the difference in the color reproduction for each of the respective illumination target regions is made less conspicuous. However, for example, when the number of LEDs is two and the number of LED illumination regions corresponding to the LEDs is also two, it is also conceivable that, near a boundary between the two LED illumination regions, a difference in colors to be reproduced is conspicuous depending on conditions.

The endoscope apparatus according to the fourth embodiment has been devised in view of such circumstances. The endoscope apparatus reduces influence of the color change near the region boundary.

Figure 8:
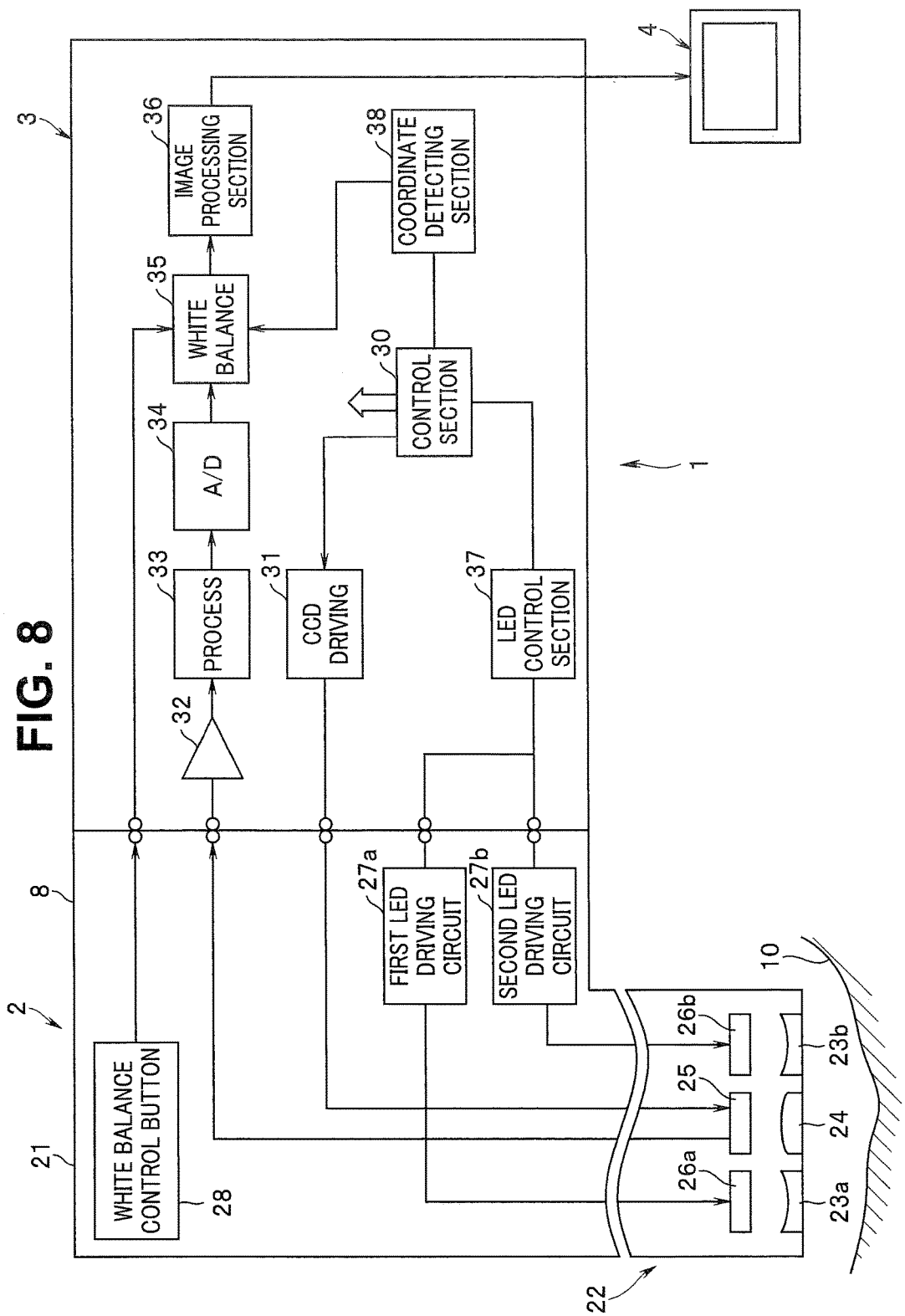
FIG. 8 is a diagram showing an overall configuration of an endoscope apparatus according to a fourth embodiment of the present invention.

FIG. 8 is a diagram showing an overall configuration of an endoscope apparatus according to a fourth embodiment of the present invention.

As shown in FIG. 8, the endoscope apparatus according to the fourth embodiment includes a coordinate detecting section 38 that is provided in the video processor 3 and detects a coordinate on an endoscopic image.

The coordinate detecting section 38 is controlled by the control section 30 to detect a coordinate on an endoscopic image related to the video signal and transmit information concerning the detected coordinate to the white balance circuit 35.

Other components in the fourth embodiment are the same as the components in the first embodiment. Only different portions are explained below. Explanation concerning portions same as the portions in the first embodiment is omitted.

White balance calculation processing in the fourth embodiment is explained with reference to FIG. 9 and FIG. 10.

Figure 9:
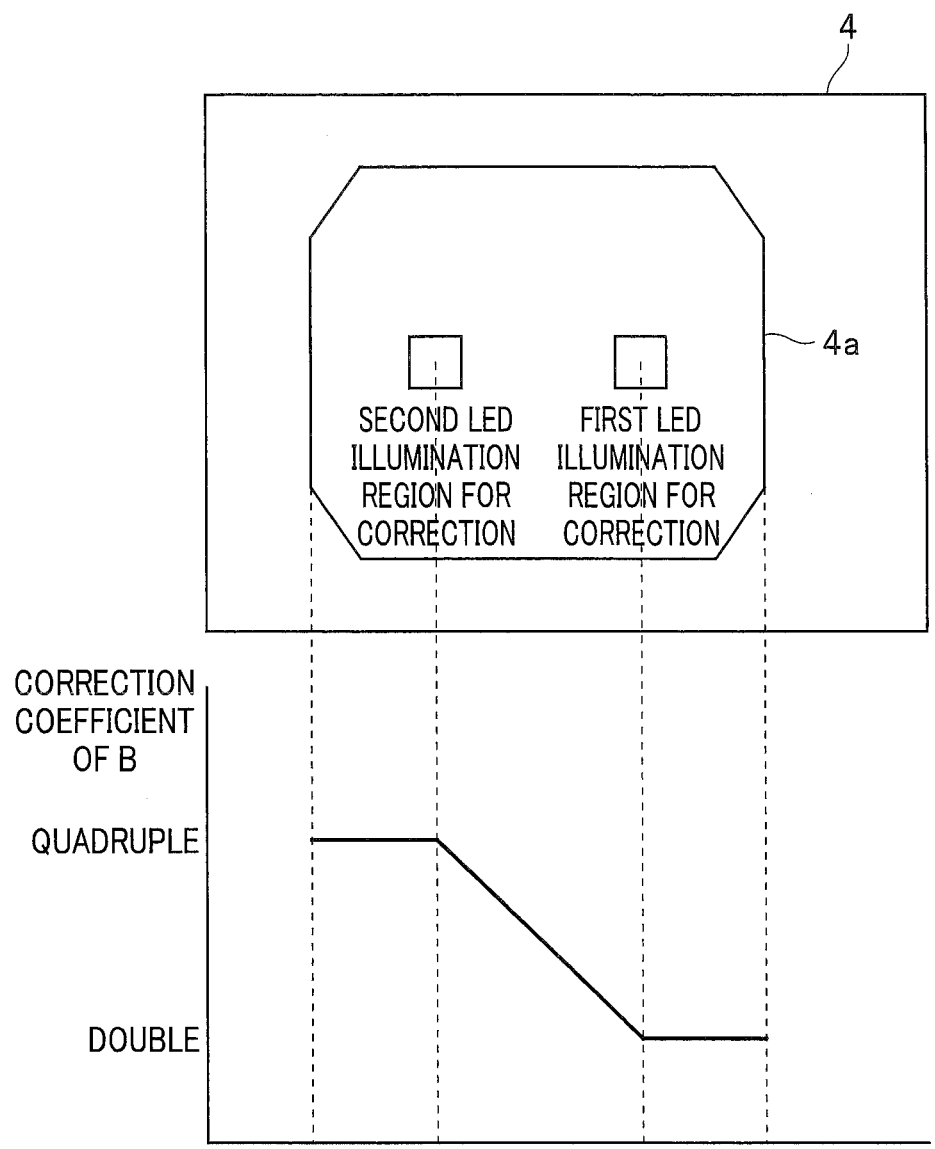
FIG. 9 is a diagram showing LED illumination regions in an endoscopic image of the endoscope apparatus according to the fourth embodiment and a relation of white balance correction coefficients between the respective LED illumination regions.

FIG. 9 is a diagram showing LED illumination regions in an endoscopic image of the endoscope apparatus according to the fourth embodiment and a relation of white balance correction coefficients between the respective LED illumination regions.

In the fourth embodiment, as in the first embodiment, the endoscope apparatus includes the two LEDs, that is, the first LED 26a and the second LED 26b as the illuminating means. The endoscope apparatus detects information for each of color components of RGB respectively in endoscopic images respectively corresponding to the illumination region (the first LED illumination region) related to the first LED 26a and the illumination region (the second LED illumination region) related to the second LED 26b.

In the first embodiment, on the endoscopic image related to the video signal, the region where illumination by the first LED 26a is relatively predominant is set as the first LED illumination region and the region where illumination by the second LED 26b is relatively predominant is set as the second LED illumination region. The entire endoscopic image is set to be occupied by the two LED illumination regions. However, in the fourth embodiment, measurement regions of color balances are respectively set as a part of the first LED illumination region and a part of the second LED illumination region.

White balance calculation processing in the fourth embodiment is explained with reference to FIG. 10.

Figure 10:
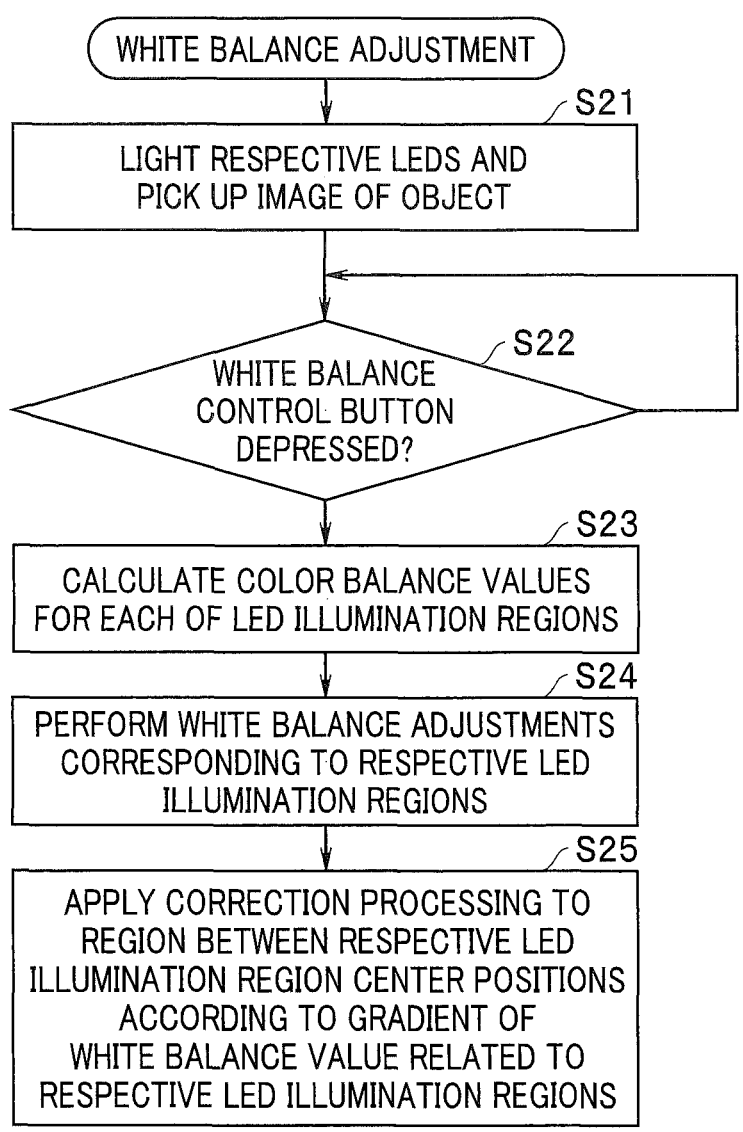
FIG. 10 is a flowchart for explaining white balance adjustment control in the endoscope apparatus according to the fourth embodiment.

FIG. 10 is a flowchart for explaining white balance adjustment control in the endoscope apparatus according to the fourth embodiment.

As shown in FIG. 10, as in the first embodiment, first, the control section 30 controls the LED control section 37 to control the first LED driving circuit 27a and the second LED driving circuit 27b, respectively lights the first LED 26a and the second LED 26b, and picks up an image of an object with the CCD 25 (step S21).

Thereafter, when the white balance control button 28 is deprssed (step S22), the white balance circuit 35 detects color information corresponding to the illumination regions of the first LED 26a and the second LED 26b in an endoscopic image (as explained above, in the fourth embodiment, a part of the first LED illumination region and a part of the second LED illumination region; the same applies below), measures color balances respectively in the first LED illumination region and the second LED illumination region, and calculates color balance values (step S23).

It is assumed that, as a result of the detection, the color information of the first LED illumination region and the color information of the second LED illumination region are respectively R:G:B=1:1:0.5 and 1:1:0.25. Then, the white balance circuit 35 executes the white balance calculation processing to multiply "B" with a coefficient of a double as the white balance calculation in a region near a center of the first LED illumination region and multiplies "B" with a coefficient of a quadruple in a region near a center of the second LED illumination region (step S24).

On the other hand, when it is assumed that the number of unit coordinate data between a center position of the first LED illumination region and a center position of the second LED illumination region is, for example, five hundred according to the coordinate position detection by the coordinate detecting section 38, the white balance circuit 35 calculates, as the following expression, a correction coefficient for a region between the center position of the first LED illumination region and the center position of the second LED illumination region (step S25).

4−(4−2)/500×(target data position−second LED illumination region center position)

In the fourth embodiment, according to the white balance calculation processing, white balance adjustments respectively corresponding to the first LED illumination region and the second LED illumination region are executed. Further, a color change near a boundary between the respective LED illumination regions can be alleviated.

As explained above, according to the fourth embodiment, even when a small number of LED illumination regions where the color balances are separately measured according to the respective LEDs are set, it is possible to perform the white balance adjustment of the entire endoscopic image without making the color change near the region boundary between the respective LED illumination regions unnatural.

Note that, in the fourth embodiment, both of the number of LEDs functioning as the illuminating means and the number of LED illumination regions where the color balances are separately measured according to the respective LEDs are two. However, the numbers are not limited to two. It is also possible to increase the numbers of LEDs and LED illumination regions and combine color balance detection results in both of longitudinal and lateral directions.

In the embodiments explained above, the LEDs, which are the light emitting elements, are adopted as the plurality of illuminating means for illuminating a subject. However, the present invention is not limited to this. A technical idea of the present invention can also be applied to an endoscope apparatus in which a plurality of light emitting elements that could cause a difference of colors in a video signal because of variation of characteristics among the plurality of light emitting elements are adopted.

Note that the present invention is not limited to the respective embodiments explained above. It goes without saying that various changes and applications are possible within a range not departing from the spirit of the invention.

(Fifth Embodiment)

An endoscope apparatus according to a fifth embodiment of the present invention is explained.

Figure 11:
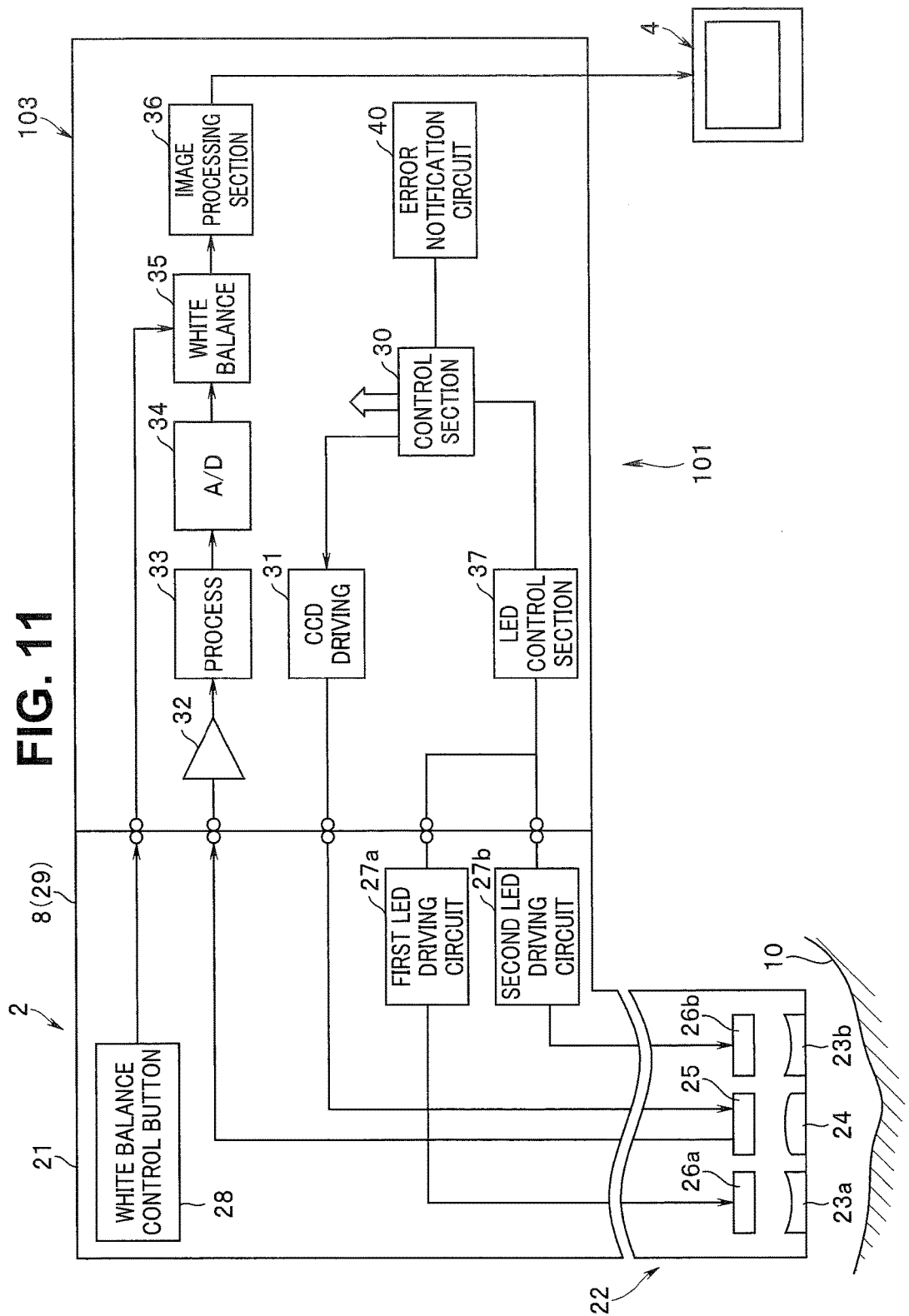
FIG. 11 is a diagram showing an overall configuration of an endoscope apparatus according to a fifth embodiment of the present invention.

FIG. 11 is a diagram showing an overall configuration of the endoscope apparatus according to the fifth embodiment of the present invention.

The endoscope apparatus according to the fifth embodiment has a characteristic in failure-time control by a video processor 103. The endoscope apparatus includes an error notification circuit 40. Other components are the same as the components in the first embodiment. Only different portions are explained below. Explanation concerning portions same as the portions in the first embodiment is omitted.

In the present embodiment, as in the first embodiment, an endoscope apparatus 101 includes, as shown in FIG. 11, the electronic endoscope 2 that is insertable into a body cavity, picks up an image of the observation target part 10 such as a diseased part in the body cavity and outputs an image pickup signal, the video processor 103 that is connected to the endoscope 2 and applies signal processing or the like to the image pickup signal outputted from the endoscope 2 to thereby output a video signal, and the monitor 4 that is connected to the video processor 103 and displays an output image corresponding to the video signal outputted from the video processor 103.

The endoscope 2 includes the elongated insertion section 22 inserted into the body cavity and the operation section 21 provided on the rear end side of the insertion section 22. The endoscope 2 is connected to the video processor 103 via the universal cord 8 extended from the operation section 21.

At the distal end portion of the insertion section 22, as in the first embodiment, the first LED 26a and the second LED 26b are symmetrically disposed across the CCD 25 as the plurality of light emitting elements for illuminating the observation target part 10 in the body cavity.

In the operation section 21, as in the first embodiment, the first LED driving circuit 27a and the second LED driving circuit 27b for respectively driving the first LED 26a and the second LED 26b are provided.

Both of the first LED driving circuit 27a and the second LED driving circuit 27b are connected to the LED control section 37 provided in the video processor 103. The first LED 26a and the second LED 26b are respectively driven and controlled by the first LED driving circuit 27a and the second LED driving circuit 27b under control by the LED control section 37.

On the distal end face of the distal end portion of the insertion section 22, the CCD 25 functioning as an image pickup device is disposed. The CCD 25 is driven according to a CCD driving signal outputted from the video processor 103. The CCD 25 photoelectrically converts an image of the observation target part 10 formed by the objective lens 24 and outputs the image as an image pickup signal.

The image pickup signal outputted from the CCD 25 is outputted to the video processor 103 via a cable 29 provided on the insides of the insertion section 22 and the universal cord 8.

Besides an image pickup signal line for the image pickup signal outputted from the CCD 25 and a driving control signal line for driving the CCD 25, power supply lines for electric power supplied from the first LED driving circuit 27a and the second LED driving circuit 27b to the first LED 26a and the second LED 26b and LED driving control lines for driving the first LED 26a and the second LED 26b are provided in the cable 29.

As in the first embodiment, the video processor 103 includes the CCD driving circuit 31 that outputs the CCD driving signal for driving the CCD 25, the amplifier 32 that amplifies the image pickup signal outputted from the CCD 25, the process circuit 33 that applies signal processing such as correlated double sampling to the image pickup signal amplified by the amplifier 32, the A/D converter 34 that applies A/D conversion to the image pickup signal processed by the process circuit 33, the white balance circuit 35 that applies white balance processing to a video signal converted by the A/D converter to thereby generate color signals including an R signal, a G signal, and a B signal, and the image processing section 36 that applies predetermined image processing to a signal outputted from the white balance circuit 35 and outputs the signal to the monitor 4.

As explained above, the LED control section 37 is provided in the video processor 103. The LED control section 37 controls the first LED driving circuit 27a and the second LED driving circuit 27b disposed in the operation section 21 of the endoscope 2.

Further, the video processor 103 includes the control section 30 that controls the amplifier 32, the process circuit 33, the A/D converter 34, the white balance circuit 35, the image processing section 36, and the like and controls the CCD driving circuit 31 and the LED control section 37.

In the present embodiment, the error notification circuit 40 is connected to the control section 30.

Characteristic action in the endoscope apparatus according to the fifth embodiment is explained.

In the present embodiment, the first LED driving circuit 27a and the second LED driving circuit 27b perform driving control (lighting, extinction, etc.) of the first LED 26a and the second LED 26b under the control by the LED control section 37. Besides, the first LED driving circuit 27a and the second LED driving circuit 27b perform monitoring of voltages and electric currents of power supply lines for supplying electric power to the first LED 26a and the second LED 26b under the control by the LED control section 37.

When the voltage values and/or the current values deviate from specified values, the first LED driving circuit 27a and the second LED driving circuit 27b send failure detection signals to the LED control section 37.

That is, when a short circuit, an overload, an opening failure, or the like occurs in the first LED 26a and the second LED 26b or the respective lines in the cable 29, it is likely that electric power that causes an overvoltage or an over current is outputted to the power supply lines extended from the first LED driving circuit 27a and the second LED driving circuit 27b.

In the present embodiment, when monitoring means in the first LED driving circuit 27a and the second LED driving circuit 27b detect that the voltage values and/or the current values deviate from the specified values, the monitoring means output the failure detection signals to the LED control section 37.

The LED control section 37, to which the failure detection signals are inputted, immediately outputs a stop signal to the first LED driving circuit 27a or the second LED driving circuit 27b related to the first LED 26a and the second LED 26b or the respective lines in the cable 29 in which the failure is detected and performs control to stop operation of the first LED driving circuit 27a or the second LED driving circuit 27b.

The LED control section 37 outputs an error notification signal to the error notification circuit 40 simultaneously with the output of the stop signal. The error notification circuit 40, which receives the error notification signal, notifies a user that a failure has occurred.

According to the present embodiment, it is possible to prevent abnormal heat generation at the endoscope distal end portion due to the failure that occurs in the LEDs for illumination disposed at the endoscope distal end or the signal cable.

(Sixth Embodiment)

An endoscope apparatus according to a sixth embodiment of the present invention is explained.

Figure 12:
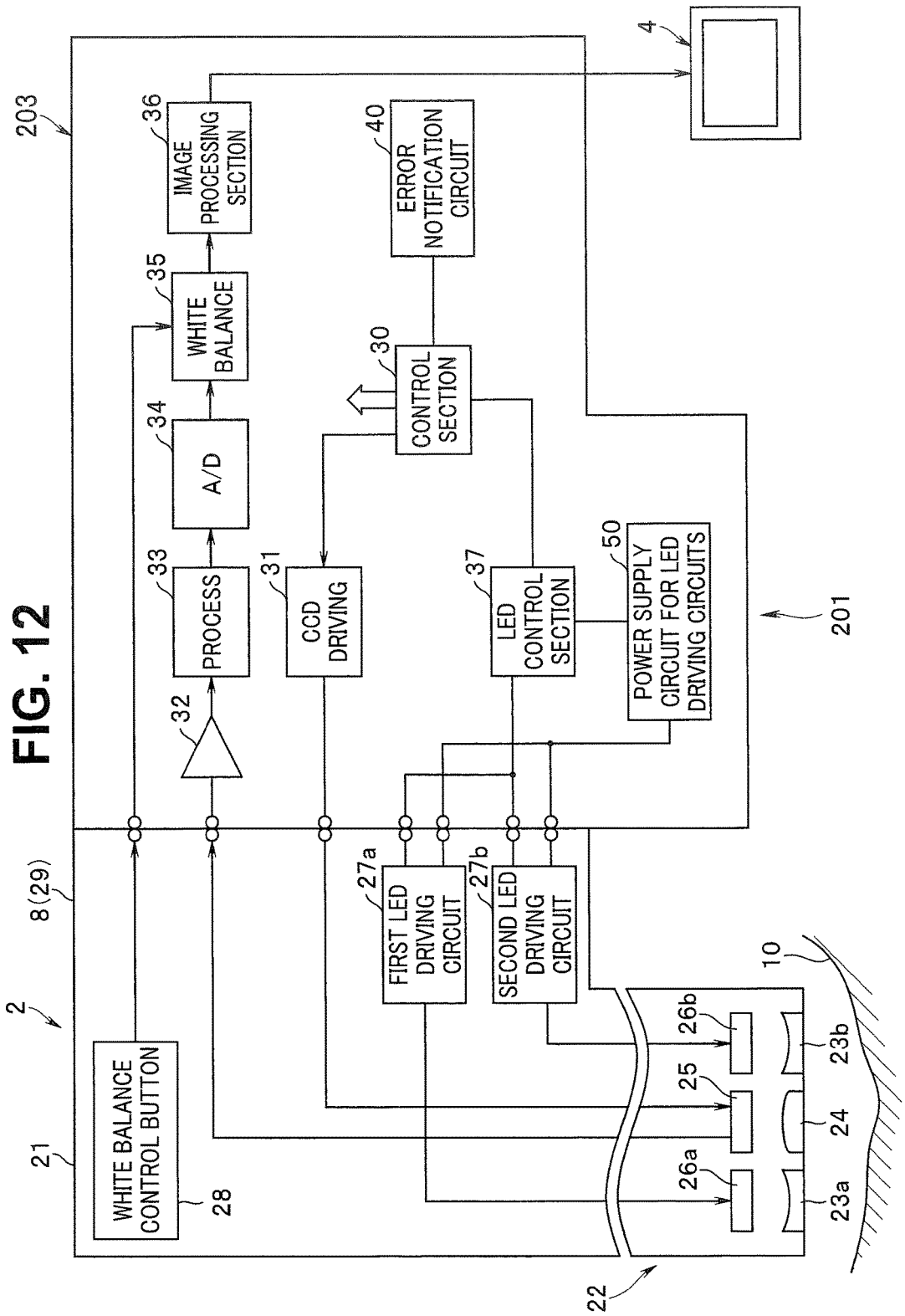
FIG. 12 is a diagram showing an overall configuration of an endoscope apparatus according to a sixth embodiment of the present invention.

FIG. 12 is a diagram showing an overall configuration of the endoscope apparatus according to the sixth embodiment of the present invention.

The endoscope apparatus according to the sixth embodiment has a characteristic in failure-time control by a video processor 203. The endoscope apparatus includes a power supply circuit for LED driving circuits 50. Other components are the same as the components in the first embodiment. Only different portions are explained below. Explanation concerning portions same as the portions in the first embodiment is omitted.

In the present embodiment, as in the first embodiment, an endoscope apparatus 201 includes, as shown in FIG. 12, the electronic endoscope 2 that is insertable into a body cavity, picks up an image of the observation target part 10 such as a diseased part in the body cavity and outputs an image pickup signal, the video processor 203 that is connected to the endoscope 2 and applies signal processing or the like to the image pickup signal outputted from the endoscope 2 to thereby output a video signal, and the monitor 4 that is connected to the video processor 203 and displays an output image corresponding to the video signal outputted from the video processor 203.

The endoscope 2 includes the elongated insertion section 22 inserted into the body cavity and the operation section 21 provided on the rear end side of the insertion section 22. The endoscope 2 is connected to the video processor 203 via the universal cord 8 extended from the operation section 21.

At the distal end portion of the insertion section 22, as in the first and fifth embodiments, the first LED 26a and the second LED 26b are symmetrically disposed across the CCD 25 as the plurality of light emitting elements for illuminating the observation target part 10 in the body cavity.

In the operation section 21, as in the first and fifth embodiments, the first LED driving circuit 27a and the second LED driving circuit 27b for respectively driving the first LED 26a and the second LED 26b are provided.

In the sixth embodiment, both of the first LED driving circuit 27a and the second LED driving circuit 27b are connected to the LED control section 37 provided in the video processor 203 and the power supply circuit for LED driving circuits 50 explained below. The first LED 26a and the second LED 26b are respectively driven and controlled by the first LED driving circuit 27a and the second LED driving circuit 27b under control by the LED control section 37.

On the distal end face of the distal end portion of the insertion section 22, the CCD 25 functioning as the image pickup device is disposed. The CCD 25 is driven according to a CCD driving signal outputted from the video processor 203. The CCD 25 photoelectrically converts an image of the observation target part 10 formed by the objective lens 24 and outputs the image as an image pickup signal.

The image pickup signal outputted from the CCD 25 is outputted to the video processor 203 via the cable 29 provided on the insides of the insertion section 22 and the universal cord 8.

Besides the image pickup signal line for the image pickup signal outputted from the CCD 25 and the driving control signal line for driving the CCD 25, the power supply lines for electric power supplied from the first LED driving circuit 27a and the second LED driving circuit 27b to the first LED 26a and the second LED 26b and LED driving control lines for driving the first LED 26a and the second LED 26b are provided in the cable 29.

As in the first embodiment, the video processor 203 includes the CCD driving circuit 31 that outputs the CCD driving signal for driving the CCD 25, the amplifier 32 that amplifies the image pickup signal outputted from the CCD 25, the process circuit 33 that applies signal processing such as correlated double sampling to the image pickup signal amplified by the amplifier 32, the A/D converter 34 that applies A/D conversion to the image pickup signal processed by the process circuit 33, the white balance circuit 35 that applies white balance processing to a video signal converted by the A/D converter to thereby generate color signals including an R signal, a G signal, and a B signal, and the image processing section 36 that applies predetermined image processing to a signal outputted from the white balance circuit 35 and outputs the signal to the monitor 4.

As explained above, the LED control section 37 is provided in the video processor 203. The LED control section 37 controls the first LED driving circuit 27a and the second LED driving circuit 27b disposed in the operation section 21 of the endoscope 2.

Further, the video processor 203 includes the control section 30 that controls the amplifier 32, the process circuit 33, the A/D converter 34, the white balance circuit 35, the image processing section 36, and the like and controls the CCD driving circuit 31 and the LED control section 37.

In the sixth embodiment, the video processor 203 includes the power supply circuit for LED driving circuits 50 that supplies electric power to the first LED driving circuit 27a and the second LED driving circuit 27b under the control by the LED control section 37.

Further, in the sixth embodiment, as in the fifth embodiment, the error notification circuit 40 is connected to the control section 30.

Characteristic action in the endoscope apparatus according to the sixth embodiment is explained.

In the present embodiment, the power supply circuit for LED driving circuits 50 performs monitoring of voltages and electric currents of the electric power supplied to the first LED driving circuit 27a and the second LED driving circuit 27b under the control by the LED control section 37.

When the voltage values and/or the current values deviate from specified values, the power supply circuit for LED driving circuits 50 sends a failure detection signal to the LED control section 37. Note that the specified values are set to different values during lighting control and during extinction control for the first LED 26a and the second LED 26b.

<Failure Detection 1>

When a short circuit, an overload, an opening failure, or the like occurs in the first LED 26a and the second LED 26b or the respective lines in the cable 29, it is likely that electric power that causes an overvoltage or an over current is outputted to the power supply lines extended from the first LED driving circuit 27a and the second LED driving circuit 27b.

In the present embodiment, when monitoring means in the power supply circuit for LED driving circuits 50 detects that the voltage values and/or the current values deviate from the specified values, the monitoring means sends the failure detection signal to the LED control section 37.

The LED control section 37, to which the failure detection signal is inputted, immediately outputs a stop signal to the first LED driving circuit 27a or the second LED driving circuit 27b related to the first LED 26a and the second LED 26b or the respective lines in the cable 29 in which the failure is detected and performs control to stop operation of the first LED driving circuit 27a or the second LED driving circuit 27b.

The LED control section 37 outputs an error notification signal to the error notification circuit 40 simultaneously with the output of the stop signal. The error notification circuit 40, which receives the error notification signal, notifies a user that a failure has occurred.

<Failure Detection 2>

On the other hand, when a failure occurs in the first LED driving circuit 27a or the second LED driving circuit 27b itself, it is also likely that electric power that causes an overvoltage or an over current is outputted to the power supply lines extended from the first LED driving circuit 27a and the second LED driving circuit 27b.

In the present embodiment, when the monitoring means in the power supply circuit for LED driving circuits 50 detects that the voltage values and/or the current values deviate from the specified values, the monitoring means sends the failure detection signal to the LED control section 37.

The LED control section 37, to which the failure detection signal is inputted, immediately outputs a stop signal to the failed first LED driving circuit 27a or the failed second LED driving circuit 27b and performs control to stop operation of the first LED driving circuit 27a or the second LED driving circuit 27b.

The LED control section 37 outputs an error notification signal to the error notification circuit 40 simultaneously with the output of the stop signal. The error notification circuit 40, which receives the error notification signal, notifies a user that a failure has occurred.

According to the sixth embodiment, it is possible to prevent abnormal heat generation at the endoscope distal end portion due to the failure that occurs in the LEDs for illumination disposed at the endoscope distal end, the signal cable, or the LED driving circuits.

(Seventh Embodiment)

An endoscope apparatus according to a seventh embodiment of the present invention is explained.

In the endoscope apparatus according to the seventh embodiment, a volatile storing section is provided in the LED control section 37 in the fifth or sixth embodiment. Other components are the same as the components in the fifth or sixth embodiment. Only different portions are explained below. Explanation concerning portions same as the portions in the fifth or sixth embodiment is omitted.

In the seventh embodiment, the volatile storing section provided in the LED control section 37 stores the failure detection information detected in the fifth or sixth embodiment. Note that this storage state is retained until a power supply of the video processor is turned on again.

The LED control section 37 always grasps a storage state of the volatile storing section and, as long as the failure detection information is stored, maintains a stop state of the first LED driving circuit 27a and/or the second LED driving circuit 27b.

That is, in the seventh embodiment, as long as the failure detection information is stored in the volatile storing section, the first LED 26a or the second LED 26b is not lit. Therefore, even when a failure occurs in the LEDs and the like, until a user recognizes the failure and the power supply of the video processor is turned on again, it is possible to prevent an endoscope from being carelessly used continuously.

(Eighth Embodiment)

An endoscope apparatus according to an eighth embodiment of the present invention is explained below.

The endoscope apparatus according to the eighth embodiment performs the failure detecting operation in the fifth, sixth, or seventh embodiment immediately after the power supply of the video processor is turned on. Other components are the same as the components in the fifth, sixth, or seventh embodiment. Only different portions are explained below. Explanation concerning portions same as the portions in the fifth, sixth, or seventh embodiment is omitted.

In the eighth embodiment, immediately after the power supply of the video processor is turned on, the first LED driving circuit 27a and the second LED driving circuit 27b respectively light the first LED 26a and the second LED 26b under control by the LED control section 37.

Thereafter, the failure detection explained above is performed in this state. When a failure is detected, the LED driving circuits are stopped to extinguish the LEDs.

In the eighth embodiment, immediately after the power supply of the video processor is turned on, it is possible to prevent abnormal heat generation at the endoscope distal end portion due to the respective failures explained above even if lighting operation for the LEDs is not performed.

(Ninth Embodiment)

An endoscope apparatus according to a ninth embodiment of the present invention is explained.

There has been known an endoscope that is mounted with an LED as illuminating means at an endoscope distal end and picks up, with an image pickup device, an image of an object illuminated by the LED.

In the endoscope of this type, an image pickup signal from the image pickup device is subjected to predetermined process signal processing in a video processor, thereafter is A/D-converted, is subjected to predetermined image processing in an image processing section after being subjected to processing such as white balance processing, and thereafter is outputted to a monitor.

When outputting a moving image video signal, the image processing section writes the AID-converted image pickup signal in a memory at any time, D/A-converts the signal written in the memory, and thereafter outputs the signal to the monitor. Consequently, it is possible to perform moving image observation of the endoscopic image.

On the other hand, when a user desires a still image, the user operates a remote switch disposed in an operation section of the endoscope. A remote control circuit in the video processor detects the operation of the remote switch. The remote control circuit, which detects a signal of the operation, stops the writing operation in the memory in the image processing section.

Consequently, the image processing section outputs a still image. The user can perform still image observation of the endoscopic image.

When the remote switch is operated again, the remote control circuit, which detects a signal of the operation, resumes the writing operation in the memory in the image processing section. Consequently, the image processing section outputs a movie again. The user can perfolin moving image observation of the endoscopic image.

In this way, in the conventional endoscope apparatus, it is possible to perform the observation of the moving image and the still image. However, when the still image is outputted, even if the LED functioning as the illuminating means is lit, illumination light of the LED is not used and electric power is wasted.

The present embodiment has been devised in view of such circumstances and it is an object of the present embodiment to provide an endoscope apparatus that does not wastefully consume electric power during an output of a still image.

Figure 13:
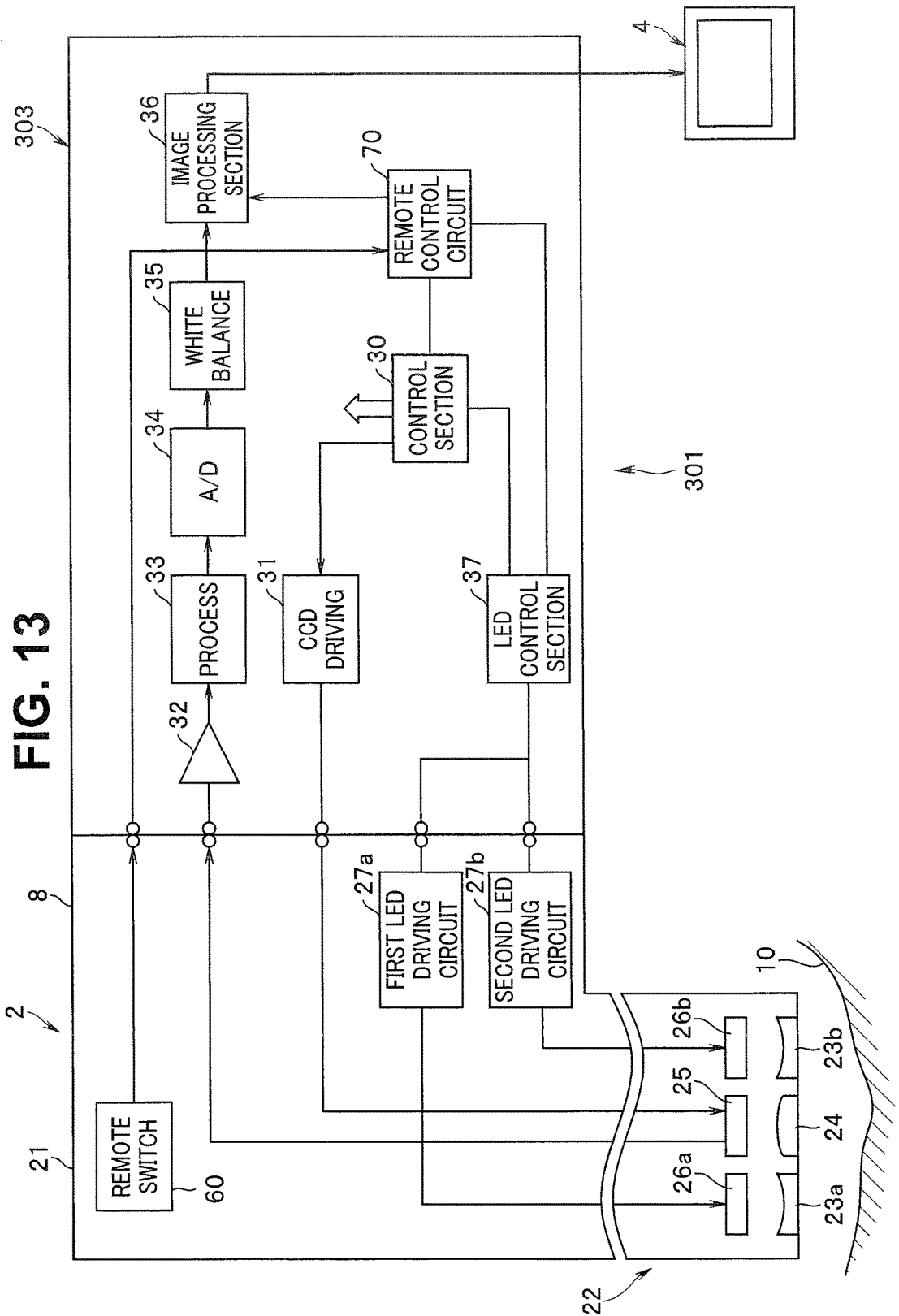
FIG. 13 is a diagram showing an overall configuration of an endoscope apparatus according to a ninth embodiment of the present invention.

FIG. 13 is a diagram showing an overall configuration of the endoscope apparatus according to the ninth embodiment of the present invention.

The endoscope apparatus according to the ninth embodiment includes a remote switch for still image reproduction in an operation section of an endoscope. Other components are the same as the components in the first embodiment. Only different portions are explained below. Explanation concerning portions same as the portions in the first embodiment is omitted.

In the present embodiment, as in the first embodiment, an endoscope apparatus 301 includes, as shown in FIG. 13, the electronic endoscope 2 that is insertable into a body cavity and picks up an image of the observation target part 10 such as a diseased part in the body cavity and outputs an image pickup signal, a video processor 303 that is connected to the endoscope 2 and applies signal processing or the like to the image pickup signal outputted from the endoscope 2 to thereby output a video signal, and the monitor 4 that is connected to the video processor 303 and displays an output image corresponding to the video signal outputted from the video processor 303.

The endoscope 2 includes the elongated insertion section 22 inserted into the body cavity and the operation section 21 provided on the rear end side of the insertion section 22. The endoscope 2 is connected to the video processor 303 via the universal cord 8 extended from the operation section 21.

At the distal end portion of the insertion section 22, as in the first embodiment, the first LED 26a and the second LED 26b are symmetrically disposed across the CCD 25 as the plurality of light emitting elements for illuminating the observation target part 10 in the body cavity.

In the operation section 21, as in the first embodiment, the first LED driving circuit 27a and the second LED driving circuit 27b for respectively driving the first LED 26a and the second LED 26b are provided.

Further, in the operation section 21, a remote switch 60 for still image reproduction is disposed. The remote switch 60 is connected to a remote control circuit 70 in the video processor 303 explained below.

Both of the first LED driving circuit 27a and the second LED driving circuit 27b are connected to the LED control section 37 provided in the video processor 303. The first LED 26a and the second LED 26b are respectively driven and controlled by the first LED driving circuit 27a and the second LED driving circuit 27b under control by the LED control section 37.

On the distal end face of the distal end portion of the insertion section 22, the CCD 25 functioning as the image pickup device is disposed. The CCD 25 is driven according to a CCD driving signal outputted from the video processor 303. The CCD 25 photoelectrically converts an image of the observation target part 10 formed by the objective lens 24 and outputs the image as an image pickup signal.

As in the first embodiment, the video processor 303 includes the CCD driving circuit 31 that outputs the CCD driving signal for driving the CCD 25, the amplifier 32 that amplifies the image pickup signal outputted from the CCD 25, the process circuit 33 that applies signal processing such as correlated double sampling to the image pickup signal amplified by the amplifier 32, the A/D converter 34 that applies A/D conversion to the image pickup signal processed by the process circuit 33, the white balance circuit 35 that applies white balance processing to a video signal converted by the AM converter to thereby generate color signals including an R signal, a G signal, and a B signal, and the image processing section 36 that applies predetermined image processing to a signal outputted from the white balance circuit 35 and outputs the signal to the monitor 4.

The image processing section 36 includes a memory that stores data of the A/D converter 34 and a D/A converter section that converts an output of the memory into a signal adapted to an external apparatus such as a monitor.

The video processor 303 includes a remote control circuit 70 that detects an input of an operation signal from the remote switch 60 and performs predetermined control according to the detection. Further, as explained above, the LED control section 37 is provided in the video processor 303. The LED control section 37 controls the first LED driving circuit 27a and the second LED driving circuit 27b disposed in the operation section 21 of the endoscope 2.

Further, the video processor 303 includes the control section 30 that controls the amplifier 32, the process circuit 33, the A/D converter 34, the white balance circuit 35, the image processing section 36, and the like and controls the CCD driving circuit 31 and the LED control section 37.

Characteristic action in the endoscope apparatus according to the ninth embodiment is explained.

In the present embodiment, an image pickup signal from the CCD 25 is subjected to predetermined process signal processing in the process circuit 33, thereafter is A/D-converted in the A/D converter 34, is subjected to predetermined white balance processing in the white balance circuit 35, and thereafter is subjected to predetermined image processing in the image processing section 36 and outputted to the monitor 4.

When outputting a moving image video signal, the image processing section 36 writes the A/D-converted image pickup signal in the memory at any time, D/A-converts the signal written in the memory, and thereafter outputs the signal to the monitor. Consequently, it is possible to perform moving image observation of the endoscopic image.

On the other hand, when a user desires a still image, the user operates the remote switch 60 disposed in the operation section 21 of the endoscope 2. The remote control circuit 70 in the video processor 303 detects the operation of the remote switch 60. The remote control circuit 70, which detects a signal of the operation, transmits the detection information to the control section 30.

Upon receiving the detection information, the control section 30 performs control to stop the writing operation in the memory in the image processing section 36.

On the other hand, the remote control circuit 70 transmits the operation detection information of the remote switch 60 to the LED control section 37 as well. The LED control section 37 controls the first LED driving circuit 27a and the second LED driving circuit 27b on the basis of the information transmitted from the remote control circuit 70 to respectively extinguish the first LED 26a and the second LED 26b.

Consequently, the image processing section 36 outputs a still image. The user can perform still image observation of the endoscopic image. On the other hand, the first LED 26a and the second LED 26b are respectively extinguished. Therefore, it is possible to prevent electric power from being wastefully consumed.

When the remote switch 60 is operated again, the remote control circuit 70, which detects a signal of the operation, transmits the detection information to the control section 30 in order to resume the writing operation in the memory in the image processing section 36.

On the other hand, the remote control circuit 70 transmits the operation detection information of the remote switch 60 to the LED control section 37 as well. The LED control section 37 controls the first LED driving circuit 27a and the second LED driving circuit 27b on the basis of the information transmitted from the remote control circuit 70 to respectively light the first LED 26a and the second LED 26b again.

Consequently, the image processing section outputs a movie again. The user can perform moving image observation of the endoscopic image.

Note that the present invention is not limited to the embodiments per se. In an implementation stage, the constituent elements can be modified and embodied in a range not departing from the spirit of the present invention. Aspects of various inventions can be formed by appropriate combinations of the plurality of constituent elements disclosed in the embodiment. For example, several constituent elements may be deleted from all the constituent elements described in the embodiments. Further, the constituent elements described in different embodiments may be combined as appropriate.

In this way, it goes without saying that various changes and applications are possible in a range not departing from the spirit of the invention.

What is claimed is:

1. An endoscope apparatus comprising:
an endoscope insertion section to be inserted into a subject;
a first light emitting element that generates first illumination light for the subject;
a second light emitting element that generates second illumination light for the subject;
a first illumination lens disposed at a distal end portion of the endoscope insertion section to emit the first illumination light to the subject;
a second illumination lens disposed at a position different from a position of the first illumination lens at the distal end portion of the endoscope insertion section to emit the second illumination light to the subject from a position different from an emitting position of the first illumination light by the first illumination lens;
an image pickup section that picks up an optical image of the subject illuminated by the first and second illumination lights;
a first color-balance measuring section that, on the basis of a video signal related to the optical image of the subject picked up by the image pickup section, measures a color balance of the video signal corresponding to a first region where illumination by the first illumination light is predominant on an endoscopic image related to the video signal and calculates a first color balance value;
a second color-balance measuring section that measures a color balance of the video signal corresponding to a second region where illumination by the second illumination light is predominant on the endoscopic image and calculates a second color balance value; and
a color-balance correcting section that applies, on the basis of the first and second color balance values, correction processing to each of the video signal corresponding to the first region and the video signal corresponding to the second region to set an entirety of the endoscopic image to a predetermined color balance.

2. The endoscope apparatus according to claim 1, wherein the color-balance correcting section performs the correction processing by adjusting coefficients of respective RGB values in an RGB color component signal related to the first color balance value calculated in the first color-balance measuring section and an RGB color component signal related to the second color balance value calculated in the second color-balance measuring section.

3. The endoscope apparatus according to claim 2, wherein the color-balance correcting section adjusts the coefficients of the RGB values to set a ratio of RGB values related to the first color balance value and a ratio of RGB values related to the second color balance value to a same ratio.

4. The endoscope apparatus according to claim 1, further comprising a coordinate detecting section that detects a coordinate on the endoscopic image related to the video signal,
wherein the color-balance correcting section applies, on the basis of a detection result of the coordinate detecting section, the correction processing to a color balance value of the video signal in a region between a predetermined position of the first region and a predetermined position of the second region.

5. The endoscope apparatus according to claim 4, wherein the color-balance correcting section applies, on the basis of the detection result of the coordinate detecting section, the correction processing to a color balance value of the video signal in a region between a center position of the first region and a center position of the second region.

6. The endoscope apparatus according to claim 5, wherein the color-balance correcting section applies, on the basis of the detection result of the coordinate detecting section, the correction processing to the color balance value of the video signal in the region between the center position of the first region and the center position of the second region according to a gradient related to a difference between the first color balance value and the second color balance value.

7. The endoscope apparatus according to claim 1, further comprising a light-emission-color control section that controls colors of illumination lights of the first light emitting element and/or the second light emitting element independently from the correction processing in the color-balance correcting section.

8. The endoscope apparatus according to claim 7, wherein the light-emission-color control section controls the colors of the illumination lights of the first light emitting element and/or the second light emitting element by changing current amounts supplied to the first light emitting element and/or the second light emitting element.

9. The endoscope apparatus according to claim 7, further comprising a coordinate detecting section that detects a coordinate on the endoscopic image related to the video signal,
wherein the color-balance correcting section applies, on the basis of a detection result of the coordinate detecting section, the correction processing to a color balance value of the video signal in a region between a predetermined position of the first region and a predetermined position of the second region.

10. The endoscope apparatus according to claim 9, wherein the color-balance correcting section applies, on the basis of the detection result of the coordinate detecting section, the correction processing to a color balance value of the video signal in a region between a center position of the first region and a center position of the second region.

11. The endoscope apparatus according to claim 10, wherein the color-balance correcting section applies, on the basis of the detection result of the coordinate detecting section, the correction processing to the color balance value of the video signal in the region between the center position of the first region and the center position of the second region according to a gradient related to a difference between the first color balance value and the second color balance value.

* * * * *